United States Patent [19]
Monks et al.

[11] Patent Number: 6,022,700
[45] Date of Patent: Feb. 8, 2000

[54] HIGH THROUGHPUT BIOLOGICAL SAMPLE PREPARATION DEVICE AND METHODS FOR USE THEREOF

[75] Inventors: Colin Monks, Idaho Springs; Karl Kilborn; Abraham Kupfer, both of Denver, all of Colo.

[73] Assignee: Intelligent Imaging Innovations, Inc., Denver, Colo.

[21] Appl. No.: 09/041,332

[22] Filed: Mar. 12, 1998

[51] Int. Cl.[7] .................................................. C12Q 1/24
[52] U.S. Cl. ............................. 435/30; 435/33; 435/40.5; 435/40.51; 435/288.4; 435/288.7; 436/63; 422/102; 359/398; 356/244
[58] Field of Search ...................... 435/4, 29, 30, 435/33, 40, 40.5, 40.51, 286.2, 286.3, 287.2, 287.3, 287.9, 288.4, 288.7, 299.1, 305.2, 305.3, 309.1, 309.4; 422/102, 104, 99; 436/528, 531, 532, 518, 63; 359/396–398; 356/246, 244

[56] References Cited

U.S. PATENT DOCUMENTS

| | | |
|---|---|---|
| Re. 34,133 | 11/1992 | Thorne . |
| 2,956,931 | 10/1960 | Goldberg . |
| 3,938,961 | 2/1976 | Lanier . |
| 4,146,365 | 3/1979 | Kay et al. . |
| 4,480,031 | 10/1984 | Shaw . |
| 4,599,315 | 7/1986 | Terasaki et al. . |
| 4,659,673 | 4/1987 | Brown . |
| 4,673,651 | 6/1987 | Rothenberg et al. . |
| 4,977,078 | 12/1990 | Niimura et al. . |
| 5,000,921 | 3/1991 | Hanaway et al. . |
| 5,023,187 | 6/1991 | Koebler et al. ........................ 436/180 |
| 5,126,276 | 6/1992 | Fish et al. . |
| 5,130,105 | 7/1992 | Carter et al. . |
| 5,231,029 | 7/1993 | Wootton et al. ........................ 435/289 |
| 5,273,905 | 12/1993 | Muller et al. ............................ 435/301 |
| 5,288,514 | 2/1994 | Ellman . |
| 5,439,649 | 8/1995 | Tseung et al. ............................ 422/99 |
| 5,482,861 | 1/1996 | Clark et al. ............................... 436/48 |
| 5,503,985 | 4/1996 | Cathey et al. ........................... 435/7.9 |
| 5,595,707 | 1/1997 | Copeland et al. ........................ 422/64 |
| 5,605,662 | 2/1997 | Heller et al. ........................... 422/68.1 |

OTHER PUBLICATIONS

Geysen et al. "Strategies for epitope analysis usig peptide synthesis." Journal of Immunological Methods. vol. 102 (1987), pp. 259–274.

*Primary Examiner*—William H. Beisner
*Attorney, Agent, or Firm*—Sheridan Ross P.C.

[57] ABSTRACT

Disclosed is a novel biological sample preparation (BSP) device and a method of using such a device that enables inexpensive and flexible high throughput sample preparation and visualization for microscopy, including high resolution, single or multi-label, 2-dimensional (2D) or 3-dimensional (3D) fluorescence microscopic observation of biological samples, such as cultured cells. Also included in the invention are a high throughput chemical sample preparation device, and a method for to clone and screen cells using a BSP device.

34 Claims, 6 Drawing Sheets

HIGH THROUGHPUT BIOLOGICAL SAMPLE PREPARATION DEVICE AND METHODS FOR USE THEREOF

FIELD OF THE INVENTION

The present invention generally relates to a novel biological sample preparation device and methods for preparation of biological samples for fluorescent microscopy that enable inexpensive and flexible high throughput sample preparation and visualization for high resolution, single or multi-label, 2-dimensional or 3-dimensional fluorescence microscopic observation of cultured cells.

BACKGROUND OF THE INVENTION

Fluorescence microscopy is a widely used tool for determining the expression and subcellular distribution of biologically relevant molecules in a variety of systems. A key word literature search of "fluorescence microscopy" reveals over 4,000 publications in the last five years alone. Despite its widespread use, however, fluorescence microscopy is generally considered to be a low throughput protocol, since it involves the careful manipulation of slides or coverslips and a number of solution changes.

The ability to perform inexpensive high throughput sample preparation for cultured cells would allow immunofluorescence microscopy to be used for a variety of new and innovative basic scientific and industrial applications, which are currently technically impractical. These include, but are not limited to, large primary antibody screens for certain localizations or behaviors, rapid hybridoma screens, fast reagent concentration optimizations for microscopy staining protocols, high throughput clone screenings for particular molecular localization phenotypes, high throughput fluorescent in situ hybridization (FISH) screens, and high throughput pharmaceutical compound efficacy screens.

Some attempts have been made to increase the throughput of tissue section sample preparation for histological staining (See, for example, Koebler, et al., 1991, U.S. Pat. No. 5,023,187; Muller, et al., 1993, U.S. Pat. No. 5,273,905; Tseung, et al., 1995, U.S. Pat. No. 5,439,649; and Wootton, et al., 1993, U.S. Pat. No. 5,231,029; each of which is incorporated by reference herein in its entirety). These technologies, however, are not appropriate for cultured cell sample preparation and do not have the throughput potential that would allow these technologies to be useful for the applications discussed above.

Therefore, there is a need in the art for a device and method for inexpensive, high throughput preparation of biological samples for fluorescent microscopy applications.

SUMMARY OF THE INVENTION

One embodiment of the present invention relates to a high throughput biological sample preparation (BSP) device. Such a device comprises: (a) a substantially planar substrate having a top and a bottom surface; and, (b) a plurality of biological support members projecting away from the top surface of the substrate and being arranged in an ordered array. Each of the biological support members has a first and second end.

The first end of the biological support member has a surface effective for attachment of a biological sample thereto. In one embodiment, the surface area is at least about 1 mm$^2$. In another embodiment, the surface area is sufficient to attach at least about 100 cells thereto. In yet another embodiment, the first end is substantially planar. In another embodiment, the first end is configured to interface with an objective lens of a microscope. Another embodiment of the present invention includes a device wherein the members have dimensions such that the first ends can be contacted with a liquid medium in a manner such that the first ends are substantially equally exposed to the liquid medium. In yet another embodiment, the first end is pretreated with a chemical that enhances attachment of the biological sample.

The second end of the biological support member is connected to the top surface of the substrate at a predetermined angle. In one embodiment, the predetermined angle is substantially 90°. In yet another embodiment, the second end is reversibly connected to the top surface of the substrate.

In one embodiment of the biological sample preparation device of the present invention, the first and said second ends of the members are separated by a distance sufficient to allow the first end of each of the members to be contacted with liquid within a well without the second end being contacted by the liquid.

The biological support members of a biological sample preparation device of the present invention can be any shape, including, but not limited to, conical and frustoconical. It is one embodiment of the present invention that the biological support members are comprised of a material that is not fluorescent. In one embodiment, the biological support members are arranged on the substrate with respect to each other in a configuration which allows the first end of each of the members to be lowered into a separate well. In another embodiment, the substrate has at least one containment means extending around a periphery of the substrate that is sufficient to contain a liquid on the top surface of the substrate. In a further embodiment, the substrate has a prop means that is sufficient to support the device when inverted onto a planar surface, such that the biological support members do not contact the planar surface. In yet another embodiment, the substrate has a handling means for handling the device without contacting the substrate or the biological support members.

In another embodiment, the biological sample preparation device includes a means for identifying (e.g., by encoding the position of) a specific biological support member on the device. Such means for identifying a position can include a bar code, a number, a letter, a color or a symbol.

In yet another embodiment, the biological sample preparation device includes a means for encoding a point of origin on a biological support member for positioning on an X-Y stage of a microscope. Such means for encoding an origin can include a bar code, a number, a letter, a color or a symbol.

In yet another embodiment of a biological sample preparation device of the present invention, such a biological sample preparation device comprises 96 biological support members, the array of members being configured so that each of the members can be placed into a separate well of a 96-well microtiter plate. In another embodiment, the device has from about 6 to about 12 biological support members, the array being configured so that each of the members can be placed into a separate well of a row of a 96-well microtiter plate. In yet another embodiment, the biological sample preparation device is configured to be handled by a micromanipulator.

Other embodiments of the biological sample preparation device of the present invention include a device which is sterilizable (e.g., autoclavable) and/or disposable.

Yet another embodiment of the present invention relates to a method for preparing a biological sample for microscopy. This method includes the steps of: (a) providing a biological sample preparation device of the present invention as described in the first embodiment above; (b) attaching a biological sample to the first end of each of the members; (c) preparing the biological sample for microscopy (e.g., fluorescence microscopy) by contacting the first ends with a series of reagents effective to visualize the biological sample by microscopy; (d) contacting the first ends that have the biological sample thereon with a medium; and, (e) visualizing the biological samples with a lens of a microscope. In one embodiment, the lens is a water immersion lens.

In one embodiment of the method of the present invention, the first end is pretreated with a compound for enhancing attachment of the biological sample to the first end prior to the step (b) of attaching.

In one embodiment of the method of the present invention, the biological sample is selected from the group of an intact cell, a cellular extract, a cellular membrane preparation, a tissue section and a nucleic acid molecule. In one embodiment, the biological sample is a cell sample. In this embodiment, the step of preparing can include the steps of fixing the cell sample, staining the cell sample, and washing the cell sample.

In another embodiment of the method of the present invention, step (b) of attaching includes attaching a different biological sample to the first end of each of the members, and step (c) of preparing includes contacting each of the first ends with an identical series of reagents. In yet another embodiment of the method of the present invention, step (b) of attaching includes attaching the same biological sample to the first end of each of the members, and step (c) of preparing includes contacting each of the first ends with a different series of reagents.

Yet another embodiment of the present invention relates to a high throughput chemical sample preparation device. Such a device includes: (a) a substantially planar substrate having a top and a bottom surface; and, (b) a plurality of chemical sample support members projecting away from the top surface of the substrate and being arranged in an ordered array. Each of the members has a first and second end, the first end having a surface effective for attachment of a chemical sample thereto, and the second end connected to the top surface of the substrate at a predetermined angle.

Another embodiment of the present invention relates to a method to clone and screen cells using a single device. Such a method includes the steps of: providing a biological sample preparation device as described in the first embodiment of the present invention above; (b) attaching about one cell to be cloned to the first end of each of the members; (c) contacting the cell with a cell culture medium; (d) culturing the cell under conditions sufficient to allow growth and division of the cell to produce a clonal population of cells, such that the cell divides to produce at least about 100 cells; (e) preparing the cells for microscopy by contacting the cells with a series of reagents effective to visualize the cells by microscopy; (f) contacting the cells with a medium for microscopy; and, (g) visualizing the cells with a lens of a microscope to screen the cells for a selection characteristic.

DETAILED DESCRIPTION OF THE INVENTION

Figure 1:
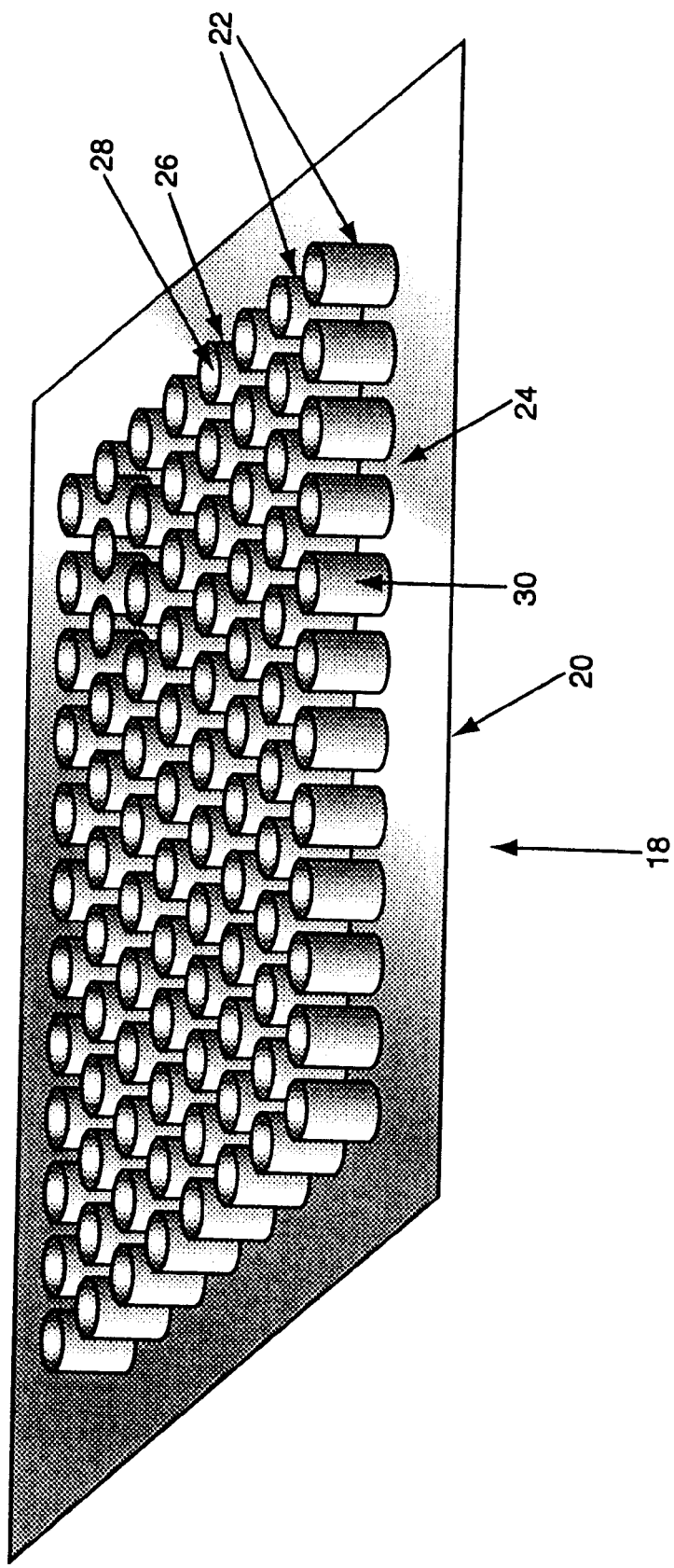
FIG. 1 is a perspective view of a biological sample preparation device of the present invention having 96 biological support members arranged in 8 parallel rows.

The present invention relates to a novel biological sample preparation (BSP) device and to a method of using such a device that enables inexpensive and flexible high throughput sample preparation and visualization for high resolution, single or multi-label, 2-dimensional (2D) or 3-dimensional (3D) fluorescence microscopic observation of biological samples, such as cultured cells. This new device and method enables microscopy, and in particular, fluorescence microscopy, to be easily used by both basic research and industry to perform a variety of novel screens and evaluations based on subcellular localization of biologically relevant molecules. Such evaluations were heretofore technically impractical. These innovative basic scientific and industrial applications for which the device and method of the present invention are particularly useful include, but are not limited to, large primary antibody screens for certain localizations or behaviors, rapid hybridoma screens, fast reagent concentration optimizations for microscopy staining protocols, high throughput clone screenings for particular molecular localization phenotypes, high throughput fluorescent in situ hybridization (FISH) screens, and high throughput pharmaceutical compound efficacy screens.

The biological sample preparation (BSP) device and method of the present invention provide several advantages over current devices and methods that are used for preparing biological samples for microscopy. In particular, the BSP device of the present invention facilitates an immense increase in sample throughput per technician. Traditional staining protocols can be performed manually at around 20–30 samples per technician per day. Using the BSP device and method of the present invention, a technician will increase manual sample throughput by at least two orders of magnitude. Furthermore, even greater sample throughput can be achieved by using the device and method of the present invention in an automated system, to which the present invention is easily adapted.

Another advantage of the BSP device and method of the present invention is that, while the sample throughput is greatly increased, the desirable fundamental flexibility of traditional fluorescence protocols is preserved. For example, using the BSP device and method of the present invention: (a) single or multiple labelings can be performed; (b) individual samples can be either all the same biological sample types (e.g., the same cell type) or different biological sample types; (c) individual samples can be treated the same or differently prior to fixation; (d) primary antibodies used in the labeling process can be either the same or different between samples; and/or, (e) additional antibodies or stains can be standardized or varied between samples.

In addition, the BSP device and method of the present invention allows expensive reagents used in the labeling process to be conserved and/or reused. More specifically, the present invention minimizes the amount of reagents required per sample per step of the labeling method. Such conservation of reagents is significant because certain reagents used in the labeling process, such as primary antibodies, tend to be limited and expensive resources. The BSP device of the present invention typically requires about 20 μl or less per sample of a primary antibody preparation at a concentration of about 10 μg/ml, and a portion of this volume is recoverable and can be reused. In contrast, traditional labeling methods used with conventional devices typically require at least about 200 μl of a primary antibody preparation of the same concentration per sample.

As discussed in detail below, another advantage of the BSP device of the present invention is that the BSP device can be configured, in one embodiment, to be compatible with all standard 96-well fluid manipulation devices such as multi-channel pipetors. Furthermore, the BSP device requires less manual dexterity to properly operate than conventional staining procedures which usually involve numerous manipulations of fragile coverslips via forceps.

The BSP device can be visualized with an immersion water lens, which provides numerous advantages over conventional microscopy methods, including the elimination of the time-consuming, costly, and tedious step of mounting of coverslips on slides.

Finally, it is within the scope of the present invention that the BSP device may itself be reusable or disposable, providing great flexibility to a research, clinical and/or industrial laboratory.

One embodiment of the present invention relates to a high throughput biological sample preparation (BSP) device. Such a device includes: (a) a substantially planar substrate having a top and a bottom surface; and, (b) a plurality of biological support members projecting away from the top surface of the substrate and being arranged in an ordered array. Each of the biological support members has a first and second end. The first end has a surface effective for attachment of a biological sample thereto, and the second end is connected to the top surface of the substrate at a predetermined angle.

According to the present invention, the substantially planar substrate of the BSP device of the present invention can have any configuration that is suitable for providing a base to which the biological support members can be connected, such as a plate. The substrate can be of any shape, including, but not limited to, rectangular, square, triangular or round, such shape typically corresponding to the arrangement of the biological support members on the top surface of the substrate. For example, if 96 biological support members are arranged in 8 parallel rows, each row having 12 members spaced equidistance apart, such that the ordered array of members is in the shape of a rectangle, then the substrate will typically be configured as a rectangle having similar dimensions to the ordered array of members. The distance between the top surface and the bottom surface of the substrate can be any distance which allows the substrate to serve as a base to which the members attach and which is easily handled by a technician. In one embodiment, the configuration of the substrate is designed to be used in an automated device, such as a device that is adapted to hold standard 96 well microtiter plates or a micromanipulator.

According to the present invention, a biological support member is the portion of the BSP device which is designed to provide a surface to which a biological sample can be attached. In addition, such surface can enable the biological sample to be cultured, manipulated (e.g., stained, washed, etc.) and/or observed microscopically. Biological support members have at least a first end and a second end. The first end has the above-mentioned surface effective for the attachment of a biological sample thereto. As such, the surface area of the first end is large enough to attach the desired biological sample, such that the intended protocol can be performed. For example, if the biological sample is a cell sample to be prepared for fluorescent microscopy, the surface area is of a size sufficient to which at least the minimum acceptable number of cells (e.g., 100 cells) can be attached, stained and visualized microscopically. If the biological sample is a tissue sample, then the surface area is of a size sufficient to attach a tissue sample thereto.

In one embodiment, the surface of the first end of the member is configured to provide a surface area of at least about 0.5 mm$^2$, and more preferably, at least about 0.75 mm$^2$, and even more preferably, at least about 1 mm$^2$, to which a biological sample can attach. If the surface of the first end is round, the diameter of the surface is preferably at least about 0.16 mm. In another embodiment, the first end is configured to provide a surface area sufficient to attach at least about 100 cells, and more preferably, at least about 500 cells, and even more preferably, at least about 1000 cells thereto.

One use of the BSP device of the present invention is the preparation and presentation of biological samples for microscopy, and in particular, fluorescence microscopy. As such, in one embodiment, the first end of the members is configured to interface with an objective lens of a microscope. Preferably, such configuration allows for the optimal resolution of the biological sample with a minimum of background fluorescence. As such, the surface of the first end can be convex, concave, or substantially planar, with a substantially planar surface being most preferred. In one embodiment of the present invention, the first end is comprised of polished glass, which is particularly suitable for microscopic applications of the BSP device.

In another embodiment of the BSP device of the present invention, the first ends are pretreated with a chemical that enhances attachment of a biological sample to the first end. Such chemical pretreatments can include, but are not limited to, poly-lysine coating, fibronectin coating, CELLTAC coating or oligonucleotide coating, antibody coating or soluble receptor coating. Such pretreatments can be used, for example, when the biological sample is a non-adherent cell. Examples of chemical pretreatment of the first end of the biological support members are described in detail in the Examples section.

The second end of the biological support member is connected to the top surface of the substrate at a predetermined angle. The predetermined angle is selected to project the members from the substrate at an angle that is compatible with the desired biological manipulations of the device. Such manipulations will be described in detail below. In one embodiment, the second end of the member is connected to the top surface of the substrate at a substantially 90° angle. The second end of the members is typically connected to the top surface of the substrate fixedly (i.e., without flexibility or wobble at the point of connection), such that the substrate and members can be handled as a single unit. It is within the scope of the present invention, however, that the connection of the second end to the substrate can be flexible or moveable, if such flexibility or moveability is desirable for using the device in a particular protocol, or for example, with a particular machine. In one embodiment, the second end is permanently attached to the substrate. In another embodiment, the second end is reversibly connected to the substrate. One advantage of having the members reversibly connected to the substrate is that the ordered array of the members on the substrate can be varied as desired, providing increased flexibility for use of the device.

In one embodiment, a single biological support member can have one second end and a plurality of first ends, such that the biological support member forms a branching member, rather than a single form, such as a cylinder or a frustoconical form. In this embodiment, a second end of a biological support member can be connected to a planar substrate, and this second end can support a plurality of first ends which branch away from said second end.

In one embodiment of the BSP device of the present invention, the biological support members preferably have dimensions such that the first ends of the members can be contacted with a liquid medium in a manner such that the first ends are substantially equally exposed to the medium. As such, all of the biological support members of a single BSP device are preferably of the same height, as measured from the first end to the second end. It is within the scope of the present invention, however, that the members can be of different heights (e.g., alternating heights) if it is desirable to have such a configuration for a given protocol. In one embodiment, the first and second ends are separated by a distance sufficient to allow the first end of each of the members to be contacted with liquid within a container, without the second end being contacted by the liquid. It is within the scope of the present invention that the distance between the first and second ends can be varied according to the desired configuration and use of the device.

Therefore, it will be apparent to one of ordinary skill in the art that by varying the height, width and shape of the biological support members within the guidance and limitations provided herein, a variety of different biological support members can be created which are adaptable to a variety of different protocols. For example, if a BSP device is to be used in conjunction with a standard 96 well microtiter plate (this embodiment is described in more detail below), then the members are preferably designed to be capable of being placed into the well of such a microtiter plate such that the biological sample can be contacted with a liquid reagent in the well of the plate. Therefore, the height, shape and width of the members in this embodiment are configured to allow this interaction to take place without creating technical problems, such as the trapping of air bubbles within the well (e.g., due to the biological support member being too large relative to the volume capacity of the well). A preferred embodiment of a biological support member configured to be used in conjunction with a standard 96 well microtiter plate is a cylindrical biological support member, having a circular first end with a diameter of from about 0.5 mm to about 5 mm, and having a distance between the first and second end (e.g., height) of from about 2 mm to about 8 mm.

As discussed above, the biological support members can be configured in any shape suitable for the intended use of the device and/or according to the aesthetic preferences of the manufacturer of the device. Such configurations include, but are not limited to, cylindrical, frustoconical, cuboidal, rectangular parralelepiped, and frustopyramidal.

According to the present invention, the biological support members can be arranged on the substrate in any ordered array, preferably corresponding to the intended use of the BSP device. In one embodiment, the members are arranged on the substrate with respect to each other in a configuration which allows the first end of each member to be lowered into a separate well. For example, in this embodiment, the members can be arranged in an array which mimics that of an assay/tissue culture plate, including a 96 well plate, a 120 well plate, a 24 well plate, a 12 well plate, or a 6 well plate, all of which are standard assay and/or tissue culture plate configurations. For example, a BSP device that is configured for use with a standard 96 well microtiter plate will typically have 96 biological support members, of a shape and size suitable for lowering into a well of such a microtiter plate (e.g., cylinders about 8 mm in height having about a 5 mm diameter), and being arranged in the same configuration as the microtiter plate.

FIG. 1 illustrates one embodiment of a biological sample preparation device of the present invention. The device shown in FIG. 1 has 96 biological support members arranged in 8 parallel rows, and is designed to be used in conjunction with a standard 96 well microtiter plate. In this embodiment, the biological sample preparation device (18) has a substantially planar substrate (20), configured as a plate, and has 96 biological support members (22) of a cylindrical shape arranged in an ordered array and projecting away from the top surface (24) of the substrate (20) at a substantially 90° angle. The first end (26) of each of the members (22) has a surface (28) effective for attachment of a biological sample, such as a cell, thereto. The second end (30) of each of the members (22) is connected to the top surface (24) of the substrate (20) at the above-described 90° angle.

Figure 2:
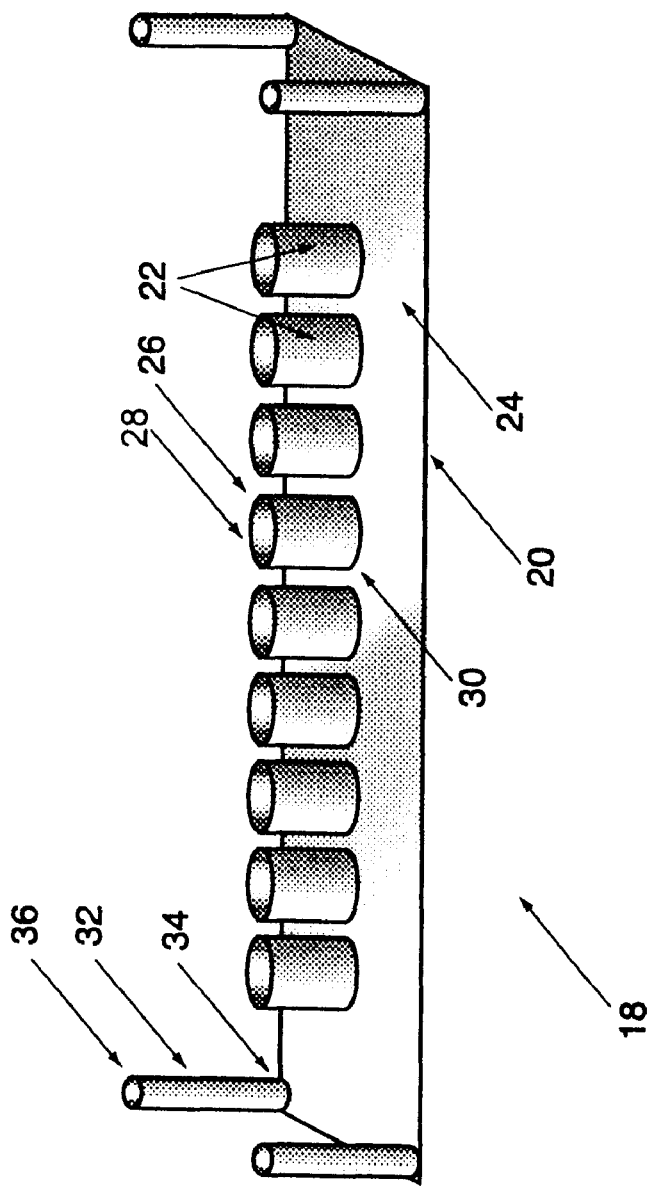
FIG. 2 is a perspective view of another biological sample preparation device of the present invention having 9 biological support members arranged in a single row.

In another embodiment, the biological support members are configured to be used in a single row of a standard assay/tissue culture plate. For example, a BSP device can have from about 6 to about 12 biological support members which are arranged so that each of the members can be placed into a separate well of a single row or column of a 96 well microtiter plate. In this example, each row or column of the 96 well plate can contain a different set of reagents, and the BSP device can be easily moved through the series of reagents by lifting the device from one row of wells and moving the device into the next row of wells. Such an embodiment of the BSP device of the present invention is illustrated in FIG. 2. FIG. 2 shows a biological sample preparation device (18) that has a substantially planar substrate (20) which is configured to be a rectangular plate. The substrate (20) has 9 biological support members (22) of a cylindrical shape arranged in an ordered array and projecting away from the top surface (24) of the substrate (20) at a substantially 90° angle, similar to the members shown in FIG. 1. The first end (26) of each of the members (22) has a surface (28) effective for attachment of a biological sample, such as a cell, thereto. The second end (30) of each of the members (22) is connected to the top surface (24) of the substrate (20) at the above-described 90° angle.

It is within the scope of the present invention that other permutations for arrangement of the members of the BSP device will be realized according to a given protocol and the materials and/or machines to be used with the BSP device in the given protocol. For example, a BSP device of the present invention can be configured to be very small, such as a size that would be useful with a micromanipulator, or of a size adapted to fit an automated machine, such as a plate washer.

Figure 3:
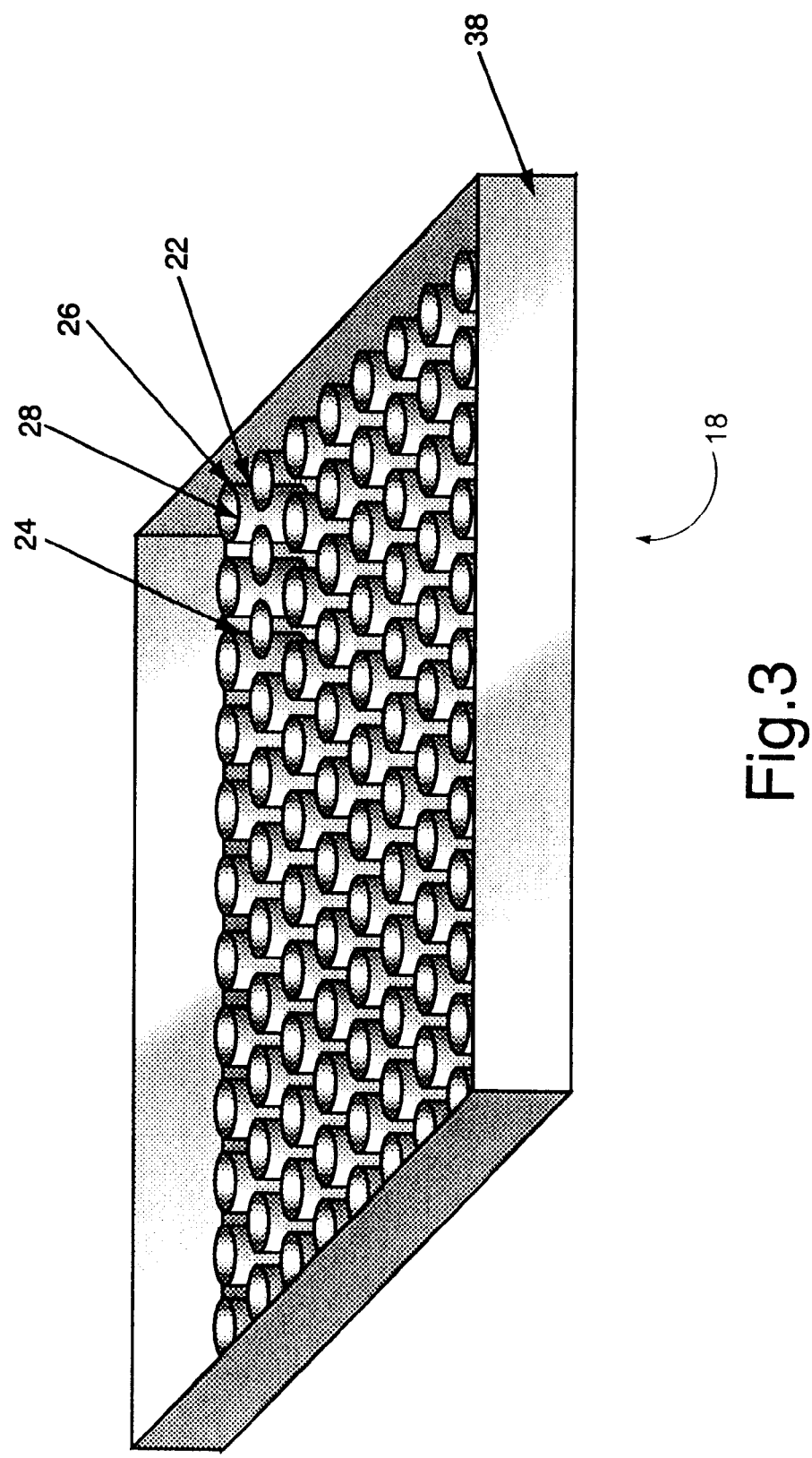
FIG. 3 is a perspective view of another biological sample preparation device of the present invention having a containment means that is sufficient to contain a liquid.

In one embodiment of a BSP device of the present invention, the substrate has at least one containment means extending around a periphery of the substrate that is sufficient to hold a liquid on the top surface of the substrate. In this embodiment, a containment means can be any structure that provides the function of holding a liquid on the top surface of the substrate. Such a containment means includes, but is not limited to, a wall which extends at a substantially 90° angle from the periphery above the top surface of the substrate. The wall can be a continuous wall around the periphery, which bends as required by the configuration of the substrate. Alternatively, the containment means can comprises two or more walls which are connected to each other, for example, at a corner of noncircular substrate. Other embodiments of the containment means are also encompassed by the present invention, such as substrates having a top surface which slopes upwardly at the periphery so that a liquid can be contained on the top surface of the substrate. Preferably, the containment means is sufficient to allow a liquid to be contained such that the surface of the first end of the biological support members can be contacted with the liquid. This embodiment provides the advantage of being able to perform various wet chemistry steps of a biological protocol (e.g., fluorescent staining) within the BSP device itself, without the need for extra pans or dishes. In other words, the biological sample on the biological support members can be contacted with liquid reagents by adding the reagents directly to the BSP device, when the device is placed, for example, with the bottom surface of the substrate resting on a laboratory bench. One embodiment of this aspect of the present invention is illustrated in FIG. 3. In this embodiment, the BSP device can be provided with a drainage means (not shown in FIG. 3) for draining liquids contained on the top surface of the substrate by the containment means as desired. Such drainage means is preferably controllable and can include, for example, one or more ports on the bottom surface or the side of the planar substrate, which is regulated by a stopper or by a valve (e.g., a stop cock).

In the embodiment of FIG. 3, the BSP device (18) is configured substantially as described in FIG. 1, but additionally has a containment means (38) which extends around the periphery of the planar substrate (20) sufficient to contain a liquid on the top surface (24) of the substrate (20). In FIG. 3, the containment means (38) is of a sufficient height to allow the surface (28) of the first ends (26) of the biological support members (22) to be contacted by a liquid. In this embodiment, since the containment means (38) is of such a height, the containment means (38) could also serve as a prop means as disclosed herein when the device (18) is inverted onto a planar surface.

In another embodiment of the BSP device of the present invention, the substrate of the device has a prop means that is sufficient to support the BSP device when the device is inverted onto a planar surface, such that the biological support members do not contact the planar surface. In this embodiment, the prop means can be any structure which is attached to the substrate in such a way that if the BSP device is inverted so that the top surface of the substrate is placed toward another planar surface, the prop means will support the device so that the biological support members (which are attached to the top surface of the substrate) do not contact the planar surface. This embodiment provides several advantages for use of the BSP device. For example, the prop means allows the BSP device to be placed into a dish or well containing a reagent used in a wet chemistry protocol by simply inverting the device into the dish so that the biological sample on the biological support members contacts the reagent while avoiding contacting the bottom of the dish. Inverting the BSP device into a liquid can allow a smaller volume of liquid to be used for a given protocol, saving valuable reagents. Similarly, a prop means can allow the device to be used with standard microtiter plates, by allowing the biological support members to contact liquid in a well of a microtiter plate, while avoiding contact with the bottom of the wells.

In this embodiment, the substrate portion of a BSP device can be fitted with a prop means on one or both surfaces of the substrate. For example, a prop means on the bottom surface of the substrate may be adapted to be used with a particular automated device that requires a plate to be held at a certain height, or by a specific mechanism to which the prop means can be adapted. In addition, a prop means on the bottom surface of the substrate can be used to provide a means by which a technician can grasp the device, such as when the device is being inverted, or "dipped" into various dishes of reagents. Other advantages of such a prop means will be appreciated by those of skill in the art and are intended to be encompassed herein.

Referring again to FIG. 2, this figure also illustrates a prop means of the present invention. In this illustration, the prop means (32) is of a cylindrical shape and has a first end (34) which is attached to the top surface (24) of the planar substrate (20) at an approximately 90° angle. Each of the second ends (36) of the prop means (32) extend away from the planar substrate (20) and have a height which is greater than the height of the biological support members (22) such that the prop means will support the biological sample preparation device (18) when the device (18) is inverted onto a planar surface, such that the biological support members (22) do not contact the planar surface.

Figure 4:
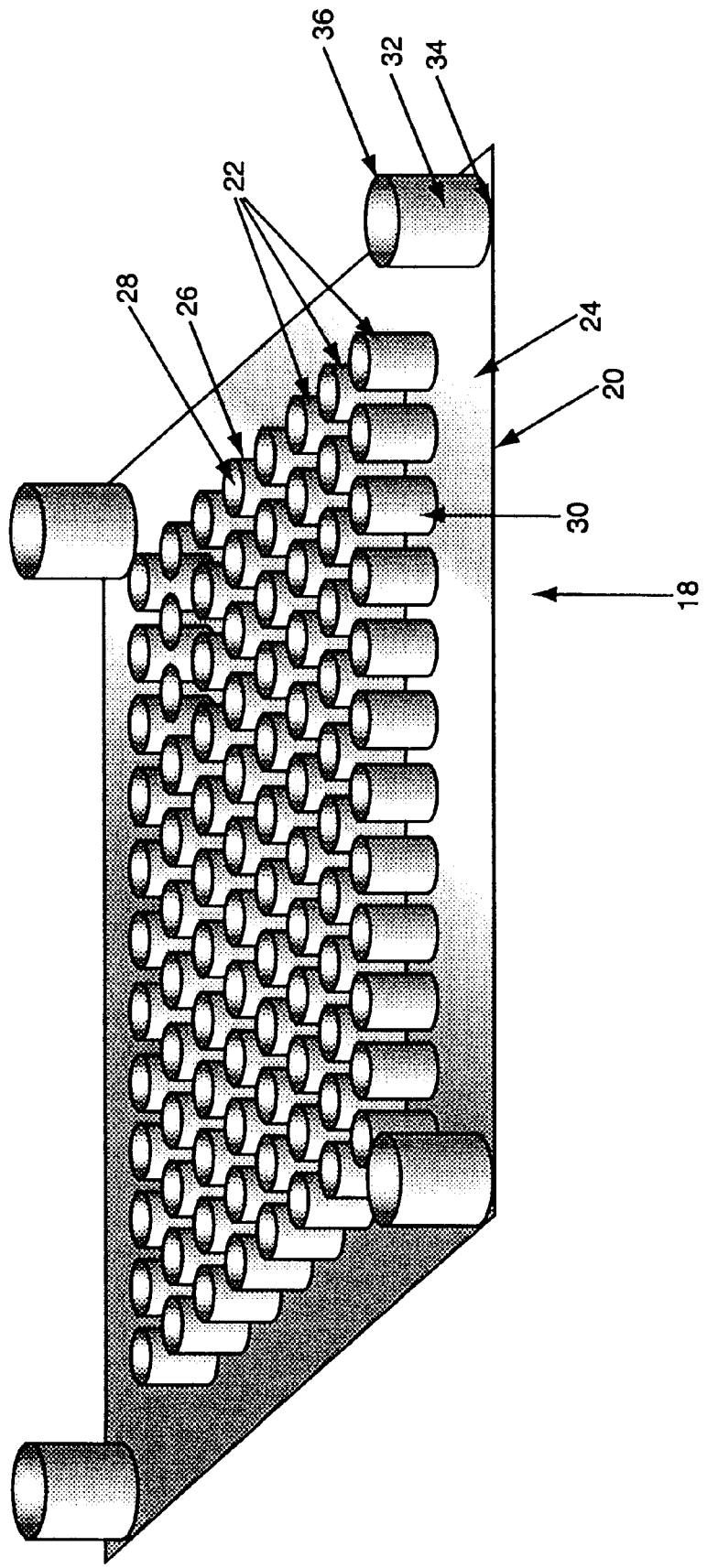
FIG. 4 is a perspective view of yet another biological sample preparation device of the present invention having a prop means sufficient to support the substrate when inverted onto a planar surface.

Another BSP device having a prop means is illustrated in FIG. 4. FIG. 4 shows a BSP device (18) having the same basic configuration as illustrated in FIG. 1. The device of FIG. 4 additionally includes a prop means (32) comprised of cylindrical feet. Similar to the prop means illustrated in FIG. 2, the prop means (32) is of a cylindrical shape and has a first end (34) which is attached to the top surface (24) of the planar substrate (20) at an approximately 90° angle. Each of the second ends (36) of the prop means (32) extend away from the planar substrate (20) and have a height which is greater than the height of the biological support members (22) such that the prop means will support the biological sample preparation device (18) when the device (18) is inverted onto a planar surface.

In yet another embodiment of the present invention, the BSP device includes a handling means which preferably allows a user to handle the BSP device without directly contacting the biological support members, and in a further embodiment, without directly contacting the planar substrate. In this embodiment, the handling means can be any means adapted to attach to, or be integral with, the BSP device, and which facilitates handling of the device (e.g., lifting and lowering the device, moving the device from one position to another). For example, a handling means can include a conventional "handle" which attaches, fixedly or removably, to the planar substrate on the top surface or sides of the device, and which forms an arch over the device. The user can grip the arch portion of the handling means to lift and carry the BSP device from position to position. In a preferred embodiment, the handling means is detachable from the device to provide flexibility and to avoid interference with the microscopic visualization of biological samples. Other handling means can include, for example, holes or indentations that are integral to the planar substrate which are adapted for the fingers of the user of the device to more securely grasp the device at the substrate. In addition, handling means can include a means which can be attached to a first device to move the device from one position to another, and then quickly and easily removed from the device so that the handling means can be used to move a second device from one position to another, and so on. Such a handling means could be, for example, a handle or hand-grip which is attached to the top surface or the sides of a planar substrate by suction or an adapted slot for securing such a handle to the device. Other embodiments of such a handling means will be appreciated by those of skill in the art.

The containment means, prop means, and handling means embodiments of the present invention make the BSP device extremely flexible in that the device can be adapted to a variety of uses and machines, as well as be handled with reduced risk of contamination of a biological sample or valuable reagent, and with less risk of accidental dropping of the device. In one embodiment of the present invention, the containment means and the prop means can be the same structure. Such a dual containment/prop means is exemplified in FIG. 3, as the containment means is of a height sufficient to allow the BSP device to be inverted onto a planar surface so that the first ends of the biological support members do not contact the planar surface.

In one embodiment of the present invention, a BSP device is configured to accept and hold in place a coverslip so that the device can be used in oil immersion microscopic applications. Such a BSP device can have, for example, a containment means as described above, which is configured such that a coverslip, which is preferably configured to correspond to the shape of the BSP device, can be carefully placed on top of the first ends of the biological support members, and preferably, held in place during microscopy. Such a configuration can include for example, a containment means as shown in FIG. 3, which is further configured with "slots" or a ledge for supporting a coverslip on the first ends.

A BSP device of the present invention can be comprised of any material suitable for use with a given biological sample and/or with a given protocol. Additionally, if the BSP device is to be used for fluorescent microscopy, then the material used for the biological support members is preferably not fluorescent. In one embodiment of the present invention, the planar substrate and the biological support members can be made of different materials.

A suitable material from which to make biological support members includes any material: (a) to which a biological sample can be attached, while maintaining the sample in a suitable condition for the intended protocol (e.g., a material for the attachment of cells that maintains the viability of the cells); (b) that can be manufactured into the desired shape and size; (c) that is compatible with reagents used in the biological protocol (e.g., doesn't chemically react with the reagents, unless such reaction is desired); and, (d) with regard to microscopic applications, that is preferably not fluorescent. Materials that are generally suitable for use in the BSP device of the present invention (both the planar substrate and the biological support members), include, but are not limited to, glass, crystal, polymers, plastic, silicon-based materials and/or metals.

In one embodiment, the biological support members of a BSP device are comprised of glass. In a further embodiment, the first ends of the members are polished glass. A preferred glass from which to construct biological support members is Pyrex. Pyrex is the easiest glass to manufacture into a variety of shapes, including cylinders, and it is same type of glass from which a standard petri dish and other glass tissue culture devices are manufactured. Additionally, Pyrex is not fluorescent. Therefore, Pyrex is ideally suited for the attachment of biological samples, in particular, cellular and tissue samples, and is compatible with high resolution fluorescent microscopy. In another embodiment of the present invention, a BSP device, and specifically, the biological support members comprise soft window glass, as is used in standard coverslips.

In another embodiment, a biological sample preparation device of the present invention comprises a means for identifying (e.g., encoding the position of) a specific biological support member on the device. More specifically, such a means for identifying is useful for tracking and/or identifying individual biological support members, thereby providing a means of locating and/or cataloging the specific sample or treatment applied to each individual member. Such means for identifying may comprise a means for encoding, for example, which can be used to manually locate a given sample. Alternatively, such means for identifying can be used in an automated system to identify and locate a given sample. According to the present invention, a means for identifying a specific biological support member on the device can include, but is not limited to, a bar code, a number, a color, a letter or a symbol. Additionally, individual biological sample preparation devices can be distinguished by a such a means for identifying. Encoding individual devices is particularly useful when multiple devices are used in a high-throughput sample preparation method, and even more particularly when an automated sample preparation method is used.

The means for identifying can be placed anywhere on the device including the biological support member and the planar substrate, and preferably, on a portion of the device where such identifying means does not interfere with the desired sample preparation and analysis. For example, a means for identifying a particular device could be placed on the top, sides, or bottom of the planar substrate, or on the side of a biological support member. A means for identifying the position of a specific biological support member can be placed on the biological support member, or directly below the member on the bottom, side or top of the planar substrate, or even on the bottom of the member, when the planar substrate is translucent. A means for identifying can include a sticker, an etching, a raised area, or any other suitable means for identifying or encoding such a position. In one embodiment, a means for identifying a specific biological support member can be etched onto the first end of the biological support member, wherein the attachment of a biological sample to this first end is not inhibited. In a preferred embodiment, such an etched means of identifying is covered with a translucent surface (i.e., a protective covering) for attaching a biological sample so that the attachment and/or treatment of such sample is not impaired.

Yet another embodiment of the device of the present invention comprises a means for encoding a point of origin on the biological support member for positioning on an X-Y stage of a microscope. In many operations for which the biological sample preparation device of the present invention is useful, it is desirable to be able to locate a position of origin on an X-Y stage of a microscope, for example, when counting cells, or noting relative positions of different portions of the sample. As such, this means of encoding an origin can serve as a reference point for the individual viewing a given sample under a microscope. Such a point of origin is particularly useful when positioning of the microscope over a given sample is automated. Such a means of encoding an origin include any of the means described above for encoding a position, including, but not limited to, a bar code, a number, a color, a letter or a symbol. In this embodiment, the means for encoding an origin is preferably located on the top end of a biological support member. Such a means for encoding can be placed on the top end using any method heretofore described (e.g., etching, with or without a protective covering).

In one embodiment, a biological sample preparation device of the present invention is comprised of a material that is sterilizable. In another embodiment a biological sample preparation device of the present invention is comprised of a material that is autoclavable. Sterilizable devices of the present invention are particularly advantageous because they can be reusable. It is yet another embodiment of the present invention that a biological sample preparation device of the present invention is disposable. As such, the BSP device, or portions thereof, can be provided in sterile or non-sterile form by the manufacturer for single-use applications.

In one embodiment of the present invention, the planar substrate and/or the biological support members can be comprised of a material that can be heated or cooled as may be desired in a given protocol for preparation of a biological sample. As such, the planar substrate can be configured for use with another device or system for heating and/or cooling the BSP device.

One embodiment of the present invention is a BSP device generally as described herein that is comprised of glass and that is compatible with a standard 96 well plate. In this embodiment, the BSP device is composed of a flat glass plate onto which 96 glass cylinders with polished flat surfaces are attached. The 96 cylinders are spaced to fit into the wells of a standard 96 well microtiter plate (see FIG. 1). In a method of using such a BSP device, a biological sample, such as cells, can either be grown on or plated on the flat ends of the 96 cylinders. If most of the wet chemistry steps of fluorescent microscopy sample preparation are the same for all samples in a single experiment, shared steps can be performed in bulk in a single dish. Alternatively, sample preparation steps which require separate treatment of the samples can be performed in individual wells of a 96 well plate by lowering the cylinders into the wells such that the sample is contacted with liquid contained within the wells. After staining, the BSP device can be immersed in saline and the top of each cylinder can be observed using a water immersion objective lens.

Another embodiment of the present invention relates to a high throughput chemical sample preparation device. This device comprises: (a) a substantially planar substrate having a top and a bottom surface; and, (b) a plurality of chemical sample support members projecting away from the top surface of the substrate and being arranged in an ordered array. Each of the members has a first and second end, the first end having a surface effective for attachment of a chemical sample thereto, and the second end connected to the top surface of the substrate at a predetermined angle. Various embodiments of a chemical sample preparation device of the present invention are the same as those already described herein for a biological sample preparation device of the present invention.

Yet another embodiment of the present invention is a method for preparing a biological sample for microscopy. This method includes the steps of: (a) providing a biological sample preparation device of the present invention as described herein; (b) attaching a biological sample to the first end of each of the biological support members; (c) preparing the biological sample for microscopy by contacting the first ends with a series of reagents effective to visualize the biological sample; (d) contacting the first ends that have the labeled biological sample thereon with a medium; and, (e) visualizing the biological samples with a lens of a microscope. In one embodiment, the lens is a water immersion lens.

Step (b) of attaching the biological sample to the biological support members can be performed by any means suitable for generally attaching a given biological sample to a culture dish or a microscope slide. For samples that are naturally adherent to a surface such as glass or plastic, the step of attaching can simply comprise contacting the surface of the first end of the member with the sample for a time sufficient to ensure the natural attachment of the sample thereto. Attachment of an adherent cell to a biological support member is described in detail in the Examples section.

In one embodiment of the method of the present invention, the first end of the biological support members is pretreated with a compound for enhancing the attachment of a biological sample to the first end. Pretreatment can be used to attach a biological sample that is not naturally adherent to a first end of a member. Such pretreatment of the first end has been previously described herein, and includes pretreatment of the first end with a chemical including, but not limited to, polylysine coating, fibronectin coating, CELL-TAC coating, oligonucleotide coating, antibody coating, and/or soluble receptor coating.

Once the biological sample is attached to the biological support member, the step of preparing a biological sample for microscopy can be performed using any standard protocol. The step of preparing includes contacting the first ends of the biological support members with a series of reagents effective to visualize the biological sample by microscopy. Such a protocol can include preparation of a sample for fluorescent microscopy. For example, in one embodiment of the method of the present invention, the biological sample is a cell sample. In this embodiment, the step of preparing can include the individual steps of fixing the cell sample, staining (i.e., labeling) the cell sample, and washing the cell sample. Such a protocol is described in detail in the Examples section.

Prior to visualization of the sample by microscopy, the samples are contacted with medium. This medium can be any medium effective for visualization of the sample by microscopy, such as a saline buffer or medium. Visualization of the sample in the present method is preferably accomplished by using an immersion water lens of a microscope. As discussed above, using an immersion water lens to visualize samples provides numerous advantages over conventional microscopy methods, including the elimination of the time-consuming, costly, and tedious step of mounting of coverslips on slides. In alternative embodiment of the method of the present invention, a biological sample prepared by the present method is visualized using an oil immersion lens. In this embodiment, after preparation of the samples, the first ends of the members of the BSP device are covered with glycerol and a large glass coverslip is placed over the entire BSP device surface. It is an embodiment of the present invention that the BSP device can be configured with a means for accepting and holding such a coverslip, as described above. In yet another embodiment of the method of the present invention, a biological sample prepared by the present method is visualized using a standard inverted light tissue culture microscope, such as a Zeiss Axiovert microscope. In a preferred embodiment of the present invention, a biological sample prepared by the present method is visualized using an Intelligent Imaging Innovations, Inc. digital confocal workstation equipped with a water immersion lens (e.g., 40× or 63×), Nomarski optics, and appropriate filters for the stain used.

According to the present invention, a biological sample useful with the BSP device and the method of the present invention, includes, but is not limited to, an intact cell, a cellular extract, a cellular membrane preparation, a tissue section and/or a nucleic acid molecule.

In the method of the present invention, each biological support member can have the same or different biological samples attached to the first end with respect to the other members. As such, all of the members of a single device can have the same biological sample attached thereto, all of the members of a single device can have different biological samples attached thereto, or subsets of the members of a single device (e.g., a row, a half-row, a column) can have the same biological sample attached thereto, with the various subsets being different. This provides tremendous flexibility in experimental design to the user of the BSP device and method of the present invention, an advantage that is not available in a high throughput protocol with conventional microscopy methods.

In one embodiment of the method of the present invention, step (b) of attaching comprises attaching a different biological sample to the first end of each of the biological support members; and step (c) of preparing comprises contacting each of the first ends with an identical series of reagents. For example, using the previously described BSP device as illustrated in FIGS. 1, 2 and/or 4, a different biological sample (e.g., a different cell type) can be attached to each of the 96 members, or to each row or column of members. Then, the entire BSP device can be placed into a dish containing a fixative, followed by a second dish containing a wash buffer, and so on until the protocol is completed. In this embodiment of the method, a BSP device as illustrated in FIG. 3 can also be used. Using the BSP device of FIG. 3, the reagent would be added directly to the BSP device, and then aspirated or poured off prior to addition of the next reagent. Therefore, using the BSP device of the present invention in this embodiment of the method of the present invention, a large variety of sample types can be screened quickly and efficiently using a single device.

In designing and optimizing experiments for use with the above embodiment of the method of the present invention, although standard protocols will typically be easily adaptable to the present method using the BSP device, the following parameters can be evaluated and adjusted accordingly. First, if the plated biological sample is a cell or tissue sample, and the cells do not survive the bulk solution changes, this would most likely be the result of an inappropriate plating surface material. In this scenario, different materials and/or chemical pretreatment approaches can be tested as discussed above. If the nuclei of the cells are not visible in a fluorescent microscopy application, this could either be due to an unacceptably low signal or high background fluorescence. If the signal is also too low on a coverslip control when a water immersion lens is used, then the water immersion optics are insufficient to image the stain. In this scenario, the water immersion lens can be substituted with a higher resolution water immersion lens. If this approach is unsuccessful, as discussed above, an alternative to the water immersion optics are oil immersion optics. To utilize oil immersion, the first ends of the members of the BSP device could be prepared for oil optics observation by covering the first ends with glycerol and placing a large glass coverslip on the entire BSP device surface. If the signal is acceptable on the coverslip control, then the concentration of the stain used with the BSP device can be increased to compensate. Finally, if the background is too high, more washing and soaking can be performed prior to observation.

In another embodiment of the method of the present invention, step (b) of attaching comprises attaching the same biological sample to said first end of each of said members, and step (c) of preparing comprises contacting each of said first ends with a different series of reagents. Again referring to the BSP device illustrated in FIG. 1 as an example, the same biological sample can be attached to each of the 96 members. In this embodiment, the BSP device can then be used in conjunction with a 96 well plate, in which each well, or series of wells, contains a different reagent. As such, the same sample can be stained for a variety of different markers, for example, using a single device in this high throughput method. It will be apparent that other BSP device configurations can be used with the methods described herein, and that innovative protocols can be constructed which include a variety of samples and a variety of reagents.

In designing and optimizing experiments in accordance with the above embodiment of a method of the present invention, the following parameters can be evaluated and optimized. First, if the reagents mix when the BSP device is manipulated by removal from the 96 well plate and placement into bulk washing steps, one modification to a standard protocol would be to prerinse the biological support members in a second 96 well plate prior to inversion and bulk washing. Alternatively, the volume of the stain in each well can be reduced. Second, if a particular stain is not visible due to an unacceptably low signal or high background fluorescence, the concentration of the stain can be increased, the number of washes can be increased and/or oil emersion microscopy can be used (described above).

The method of the present invention can be used for a variety of research and industrial applications for which high throughput sample preparation is desirable. These methods include, but are not limited to, large primary antibody screens for certain localizations or behaviors, rapid hybridoma screens, fast reagent concentration optimizations for microscopy staining protocols, high throughput clone screenings for particular molecular localization phenotypes, high throughput fluorescent in situ hybridization (FISH) screens, and high throughput pharmaceutical compound efficacy screens. In particular, the method of the present invention is useful for preparing a biological sample for a type of fluorescent microscopy selected from the group of single-label fluorescent microscopy, multiple-label fluorescent microscopy, 2-dimensional fluorescent microscopy, 3-dimensional fluorescent microscopy and fluorescence in situ hybridization.

Yet another embodiment of the present invention relates to a method to clone and screen cells using a single device. This method includes the steps of: (a) providing a biological sample preparation device of the present invention as described herein; (b) attaching about one cell to be cloned to the first end of each of the members; (c) contacting the cell with a cell culture medium; (d) culturing the cell under conditions sufficient to allow growth and division of the cell into a clonal population of cells, such that the cell divides to produce at least about 100 cells; (e) preparing the cells for microscopy by contacting the cells with a series of reagents effective to visualize the cells by microscopy; (f) contacting the cells with a medium for microscopy; and, (g) visualizing the cells with a lens of a microscope to screen the cells for a selection characteristic. In one embodiment, the lens is a water immersion lens.

This cloning and screening method of the present invention is advantageous over previously described cloning methods because, using the BSP device of the present invention, the cloning and screening steps can be performed in a single device, allowing the high throughput methods described herein to be applied to the conventionally tedious process of cloning, screening and selecting cells. This method is particularly advantageous, for example, for screening T and B cell hybridomas, a process in which thousands of clones may be screened before the desired clone is selected.

According to the present invention, the method to clone and screen cells using the BSP device of the present invention can be applied to any cell type that is suitable for cloning. Such suitable cell types include, for example, mammalian cells and hybridomas made with such cells. Particularly preferred cell types for use with the cloning and screening method of the present invention include T lymphocytes, T cell hybridomas, B cell hybridomas, or any other cell type that is suitable for cloning. The cells to be cloned are attached to the first end of a biological support member of a BSP device of the present invention by any suitable method as described previously herein. The cells are attached to the biological support member at about 1 cell per biological support member. In order to achieve such a concentration, the cells can be attached to the biological support members by any method, such as by attachment of the cells by a manually or computer operated micromanipulator. Alternatively, a volume of medium containing the cells to be cloned can be applied to the first end of the biological support member at a concentration which will be likely to provide an average of about 1 cell per biological support member. In this embodiment, the concentration of cells initially applied to the device can be varied (e.g., about 0.3 cells/member, about 1 cell/member, about 3 cells/member, etc.) as may be necessary to achieve a high frequency of biological support members receiving about one, attached, viable cell which develops into a clonal population. Cloning techniques are well known in the art and any such cloning technique is intended to be encompassed by the present invention.

The step of contacting the cells with cell culture medium can be accomplished by any means of contacting the first ends of the biological support members with a liquid. Many such methods have been described herein and include, immersing the device in a bath of medium, inverting the device having a prop means into a bath of medium, filling the device having a containment means with medium, and/or inverting the device into a standard culture/microtiter plate having individual wells containing medium. Using the latter of these methods, it is possible to use different culture mediums on different cloning samples, providing great flexibility to the cloning procedure. A suitable, or effective, culture medium refers to any medium in which a cell to be cloned is capable of cell growth and division. Such a medium is typically a liquid medium comprising growth factors and assimilable carbon, nitrogen and phosphate sources, as well as appropriate salts, minerals, metals and other nutrients, such as vitamins. Selection of an appropriate medium can be easily made by one of ordinary skill in the art based on the specific cell type to be cloned.

In the next step of the cloning method of the present invention, the cells are cultured under conditions sufficient to allow growth and division of the cells into clonal populations. Preferably, the cells are allowed to divide to produce a number of cells suitable for screening using the BSP device and methods described herein. As such, the cells are typically allowed to divide into a clonal population of at least about 100 cells prior to screening. As used herein, suitable culture conditions include a temperature, pH and oxygen content appropriate for the cloned cell. Indeed, one of the advantages of the present invention is that conventional mediums and culture conditions can be used with the BSP device. Determining such culturing conditions are within the expertise of one of ordinary skill in the art.

The next steps of preparing the cells for microscopy (e.g., fluorescent microscopy) and visualizing the cells have been previously described herein. Alternatively, any other method of screening cells that is compatible with the BSP device can be used. The purpose of this step of the method is to screen the cells for one or more particular selection characteristics which enables the user to identify and select the desired clonal cell population(s). Such a selection characteristic can be any identifiable cellular characteristic which identifies the desired cell population, and includes, but is not limited to, expression of a cell surface marker, expression of any cell marker, a particular arrangement of a cellular component (i.e., cellular matrix or organelles), and the ability of the cell to form conjugates with another cell. Again, the BSP device of the present invention provides the advantage of allowing the cloning and screening of clones on a single device. Prior to the step of preparing the cells, if the procedure will render the cells unusable for further culture, a sample of the cells can be removed from the BSP device by any method and placed in a culture dish or microtiter plate, for example until the selection process is completed.

The following examples are provided for the purposes of illustration and are not intended to limit the scope of the present invention.

EXAMPLES

The following experiments were designed to test, in an increasingly stringent fashion, the utility of the BSP device and method of using the device.

These experiments demonstrate that the BSP device and method of using the device are compatible with fluorescence microscopy sample preparation biology, chemistry, and imaging. These experiments further show protocols for a variety of applications for the BSP device, including multi-labeling experiments, fluorescent in situ hybridization (FISH), and multiple pre-fixation treatment experiments.

Example 1

This example describes the production of a biological sample preparation device of the present invention.

The following BSP device was produced as described below and served as the prototype device for the experiments described in Examples 2–6. The BSP device was constructed from Pyrex glass cylinders having a distance from first end to second end of 8 mm long (e.g., the height of the members), and a diameter of the first end of 5 mm. The first ends were flat, polished surfaces, and the second ends were glued to a flat glass plate, (i.e., the planar substrate). The cylinders were custom made by Adams and Chittenden Scientific Glass (Berkeley, Calif.), according to the specific instructions provided by the present inventors.

Example 2

This example demonstrates that a biological sample comprising adherent cells can be attached to the BSP device and without significant loss of viability and at a density suitable for fluorescent microscopy staining protocols.

Almost all fluorescence microscopy staining protocols are performed using coverslips. Coverslips are standardly used in most microscopy laboratories for microscopy sample preparation. The coverslip samples described in all of the experiments outlined in Examples 2–8 below serve as controls for proper preparation technique. If the coverslips did not behave as expected, then there was a technical error or tissue culture difficulty that required reperforming the experiment.

There are two basic types of tissue culture cells: adherent and non-adherent. This experiment demonstrates that the device and method of the present invention can be used with non-adherent cells, and Example 3 describes how the device and method of the present invention can be used with adherent cells.

A typical non-adherent cell is a lymphocyte which can be directly isolated from animals or grown in suspension. A common lymphocyte model cell is the CH 12.LX (LoCascio et al., 1984). The following experiment is a straightforward assay of the BSP device's ability to support CH12 plating on poly-D-lysine coated cylinder ends.

CH12.LX cells were resuspended at $1 \times 10^7$ cells/ml. 40 $\mu$l of the cell suspension was plated on each cylinder end of a BSP device as described in Example 1, which was soaked overnight in a 100 pg/ml poly-D-lysine solution (this is the standard treatment for coverslips). 200 $\mu$l of the cell suspension (the equivalent volume per surface area) was plated, in parallel, on a similarly poly-D-lysine treated #1 coverslip. The cells were incubated on the BSP device cylinder ends and the coverslip for 10 minutes at 37° C. Then the coverslips and BSP device were submerged in DME medium+ 10% fetal calf serum and scored for number and viability (by 0.1% trypan blue exclusion) using a 10× objective lens mounted on a standard Zeiss Axiovert light tissue culture microscope.

Figure 5:
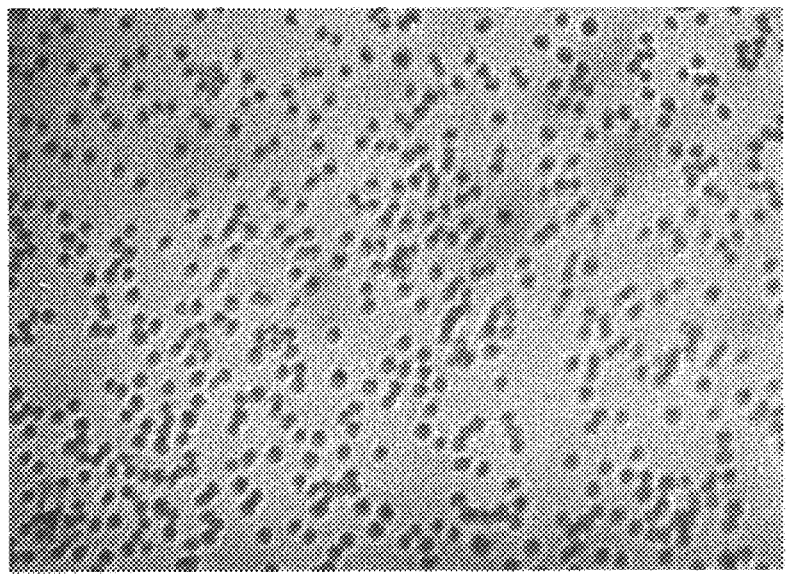
FIG. 5 is a digital image of adherent cells plated on a biological sample preparation device, imaged with a 10× objective lens mounted on a Zeiss Axiovert microscope.

The bulk and viable (non-blue) number of cells per field were counted for both the coverslip and the BSP device. FIG. 5 shows the image of the viable CH12.LX cells on the BSP device; the density of viable cells was approximately the same density as the cells plated on the coverslip (data not shown), demonstrating that the BSP device of the present invention can be utilized with non-adherent cells without adjustment of the conventional protocol.

This example and Example 3 below were designed to demonstrate that adherent cells can be grown directly on the BSP device and that non-adherent cells can be plated on an appropriately coated BSP device. The results presented in this example show that the BSP device will be usable for the various applications mentioned previously herein.

Example 3

This example demonstrates that a biological sample comprising adherent cells can be attached to the BSP device without significant loss of viability and at a density suitable for fluorescent microscopy staining protocols.

A typical adherent cell is a fibroblast, which can be grown on both tissue-culture treated plastic and glass surfaces. One of the best characterized fibroblasts is the NIH 3T3 cell (Jainchill et al., 1969). The following experiment was a straightforward assay of the BSP device's ability to support NIH 3T3 cell culture.

NIH 3T3 cells (publicly available, for example, from the American Type Culture Collection in Rockville, Md., as ATCC CRL 1658) were removed from a tissue culture flask by trypsinization and resuspended in Dulbecco's Modified Eagle's (DME) medium containing 10% fetal calf serum at a concentration of $5 \times 10^7$ cells/ml. DME is the medium recommended by the ATCC for this type of cell. 40 $\mu$l of the cell suspension were plated on each cylinder of a sterile BSP device as described in Example 1. BSP device sterilization was performed by autoclaving. 200 $\mu$l of the cell suspension (the equivalent volume per surface area) was plated on a standard #1 glass coverslip placed in a 35 mm dish. The cells were incubated on the coverslip and BSP device for 1 hour at 37° C. Then the coverslip and BSP device were submerged in DME medium+10% fetal calf serum and grown overnight at 37° C. in an incubator at 5% $CO_2$. The next day, the cells that grew on both the coverslip and BSP device were scored for number and viability using trypan blue and a 10× objective lens mounted on a standard light tissue culture microscope as described above in Example 2.

The bulk number of cells and the number of cells excluding trypan blue per field were counted for both the coverslip and the BSP device. The density of viable (non-blue) NIH 3T3 cells on the BSP device was approximately the same density as the cells plated on the coverslip (data not shown), demonstrating that the BSP device of the present invention can be utilized with adherent cells without adjustment of the conventional protocol.

Example 4

The following Example demonstrates that the BSP device of the present invention is compatible with standard sample preparation wet chemistry. This Example also shows that water immersion optics can be used for medium resolution imaging cells on the BSP device.

Most of the wet chemistry steps of a fluorescent microscopy sample preparation are the same for all samples in a single experiment. These usually include fixation, membrane permeabilization, blocking, and shared fluorescent stain treatments. Therefore, the BSP device must be compatible with these types of wet chemistry. To test the device's compatibility a simple 8 solution change DNA stain experiment was performed and the stain was evaluated for visibility with a fluorescent microscope.

It is noted that this experiment using the device described in Example 1 was performed in parallel with a second BSP device which had cylinders having a first end of about 6 mm in diameter (the device in Example 1 has a 5 mm diameter). The 6 mm cylinders fit into the wells of a standard 96 well plate too tightly to allow trapped air bubbles to escape the well. The trapped air prevented the correct contact with solutions in the wells. The 5 mm cylinders of the device described in Example 1 did not have this problem, and therefore, the 5 mm device was selected for further experiments in which submersion in the wells of a 96 well plate was required.

CH12.LX cells were plated on poly-D-lysine coated BSP device cylinder ends and coverslips as described in Example 2. Cells on coverslips and the BSP device were fixed (3% paraformaldehyde, 3% sucrose, 1× Phosphate Buffered Saline (PBS)) for 10 minutes at room temperature. The BSP device fixation, and other bulk solution steps, were performed in a Pyrex dish that was large enough to submerge the entire device. More specifically, the cylinder ends were oriented upward and the solution was added to the side of the dish to prevent the fluid stream from blasting the cells off of the device. Coverslip bulk solution steps were performed similarly in small culture dishes as is standard practice in many laboratories.

After removing the fixative by aspiration, coverslips and the BSP device were extensively washed in PBS. After the washings, the coverslips and the BSP device were treated with 0.2% Triton xIO0 in PBS for 5 minutes to permeabilize the cell membranes. This step was followed by extensive washings of the coverslips and the BSP device in PBS, as described above. The coverslips and the BSP device were then incubated in DME tissue culture media+10% fetal calf serum for 20 minutes to reduce non-specific stain binding.

In order to prepare the samples for Hoechst imaging, coverslips and the BSP device were incubated in DME tissue culture media+10% fetal calf serum containing 10 µg/ml Hoechst-33258 (Molecular Probes Inc., Eugene, Oreg.) stain for 1 hour. Following the Hoechst incubation, the samples were washed in PBS and then soaked in PBS for 2 hours prior to observation.

Figure 6:
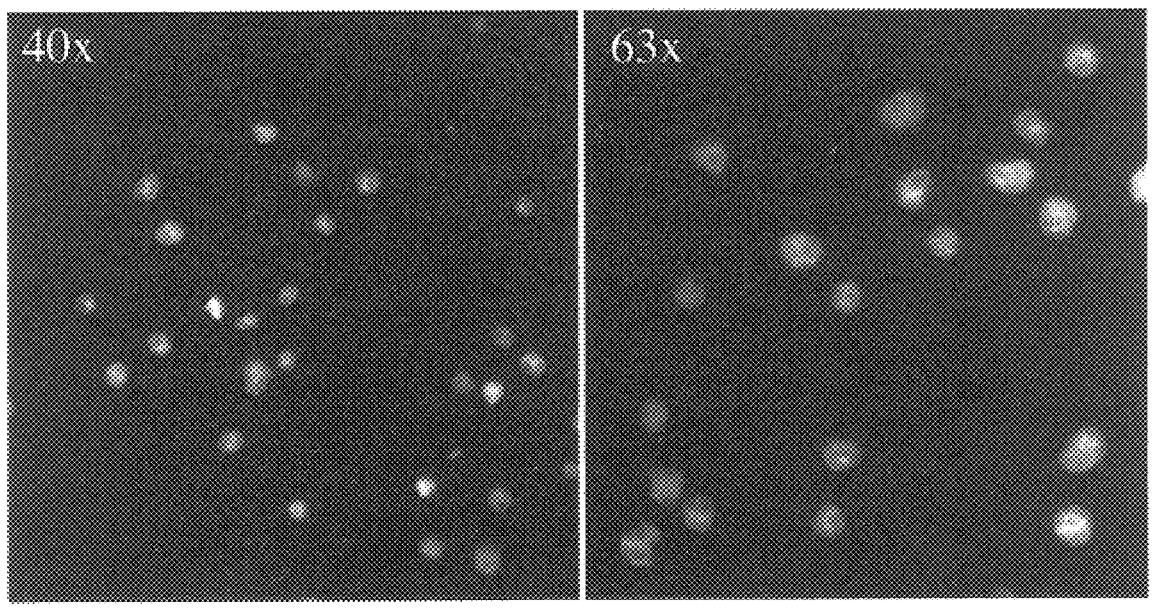
FIG. 6 is a digital image of Hoechst stained adherent cells on a biological sample preparation device, imaged with an Intelligent Imaging Innovations, Inc. digital confocal workstation equipped with a 40× (left) or a 63× (right) Zeiss water immersion objective lens.

To analyze the stainings, the coverslips and the BSP device cylinder ends were observed on an Intelligent Imaging Innovations, Inc. digital confocal workstation equipped with 40x and 63x Zeiss water immersion objective lenses, Nomarski optics, and appropriate Hoechst filters. Digital images of each condition were recorded for evaluation. The number of nuclei visible with Hoechst were compared to the number of visible cells by Nomarski optics for both the BSP device and coverslips. For coverslips mounted in glycerol, this number neared 100%. FIG. 6 shows the images collected for the BSP device using the 40x Zeiss water immersion objective lens (left panel) and the 63x Zeiss water immersion objective lens (right panel). The results from this experiment were of the same quality as the coverslip controls (data not shown).

Therefore, the BSP device of the present invention is compatible with single histological staining procedures. More particularly, this experiment showed that bulk sample preparation steps are compatible with the BSP device. This experiment also showed that water immersion observation is compatible with the BSP device. Finally, these results provide evidence that the BSP approach will be useful in scenarios where the staining is similar in all of the biological support members, but the wherein the cells on each cylinder are unique.

Example 5

The following Example demonstrates that double staining chemistries can be performed using the BSP device of the present invention.

This experiment was designed to confirm that the BSP device of the present invention can be used for multiple-labeling protocols. The two stains used in this experiment, FITC-WGA and Hoechst, show very different staining patterns and are optically separable with the correct filters. As in the previous examples, individually stained coverslips were used as a control for proper staining.

CHI2.LX cells were plated on poly-D-lysine coated BSP device cylinder ends and coverslips as described in Examples 2 and 4. The cells on the BSP device and coverslips were fixed as described previously in Example 4. After removing the fixative by aspiration, the BSP device and coverslips were extensively washed in phosphate buffered saline (PBS) as in Example 4. Also as described in Example 4, the BSP device and coverslips were treated with 0.2% Triton x100 in PBS for 5 minutes to permeabilize membranes. After further PBS washings as previously described, the BSP device and coverslips were incubated in DME tissue culture media+10% fetal calf serum for 20 minutes to reduce non-specific stain binding.

The individual cylinders of the BSP device were incubated in 20 µl of DME tissue culture media+10% fetal calf serum containing 10 µg/ml Hoechst-33258 stain for 1 hour. The incubation was performed in the individual wells of a 96 well plate. Coverslips were incubated in 100 µl of the FITC-WGA and Hoechst solutions. As described in Example 4, the BSP device and coverslips were extensively washed and then incubated in 20 µl of DME tissue culture media+10% fetal calf serum containing 20 µg/ml FITC conjugated wheat germ agglutinin (Molecular Probes Inc., Eugene, Oreg.). The BSP device and coverslips were then extensively washed and then soaked in PBS for 2 hours prior to observation.

The BSP device cylinder ends and coverslips were observed on an Intelligent Imaging Innovations, Inc. digital confocal workstation equipped with a 63x Zeiss water immersion lens, Nomarski optics, and appropriate Hoechst and FITC (ChromaTechnology Inc., Brattleboro, Vt.) filters as in Example 4. These filters are specifically designed to eliminate fluorescence bleedthrough of one probe into the other. Digital images from each condition were recorded for evaluation.

Figure 7:
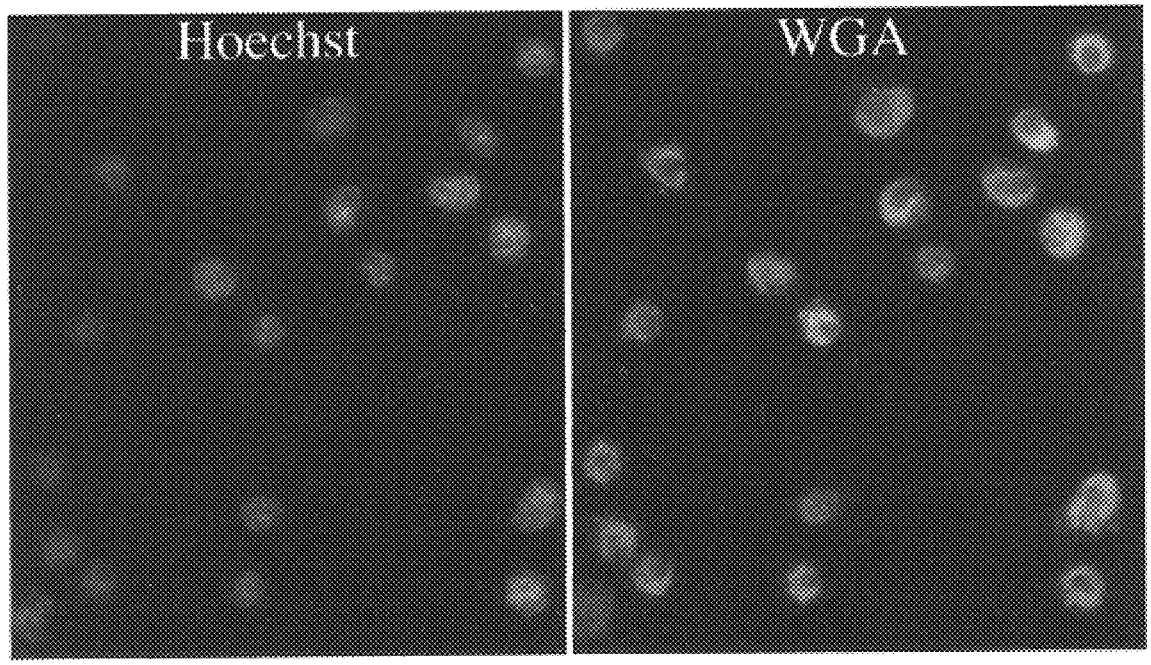
FIG. 7 is a digital image of adherent cells double stained with wheat germ agglutinin and Hoechst on a biological sample preparation device, imaged with an Intelligent Imaging Innovations, Inc. digital confocal workstation equipped with a 63× Zeiss water immersion objective lens.

The cylinders of the BSP device were evaluated for Hoechst and WGA staining. Demonstrating that the BSP device performed correctly, FIG. 7 shows that the BSP device is compatible with multiple histological staining procedures.

Example 6

This Example shows that the BSP device of the present invention is compatible with complex, multi-solution staining procedures.

CHI2.LX cells were plated on poly-D-lysine coated BSP device cylinder ends of a BSP device described in Example 1 and coverslips using the protocol described in Examples 2 and 4. The cells on the BSP device and coverslips were fixed as described previously in Example 4. After removing the fixative by aspiration, the BSP device and coverslips were extensively washed in phosphate buffered saline (PBS) as in Example 4. Also as described in Example 4, the BSP device and coverslips were treated with 0.2% Triton x100 in PBS for 5 minutes to permeabilize membranes. After further PBS washings as previously described, the BSP device and coverslips were incubated in DME tissue culture media+10% fetal calf serum for 20 minutes to reduce non-specific stain binding.

Individual coverslips were incubated in the primary antibody, rabbit anti-tubulin (Kupfer et al., 1986) for 1 hour at room temperature. Following the incubation, the coverslips and the FPS device were extensively washed in PBS as described in Example 4 above. The coverslips and BSP device cylinders were then incubated in CY3 conjugated donkey anti-rabbit antibody (Jackson ImmunoResearch Laboratories, West Grove, Pa.) for 1 hour at room temperature. Following this incubation, the coverslips and the BSP device were washed extensively with PBS as described in Example 4.

The coverslips and BSP device cylinders were then incubated in CY3 conjugated streptavidin (Jackson ImmunoResearch Laboratories, West Grove, Pa.) for 1 hour at room temperature. Following this incubation, the coverslips and BSP device were washed in PBS and soaked in PBS overnight to reduce background.

Figure 8:
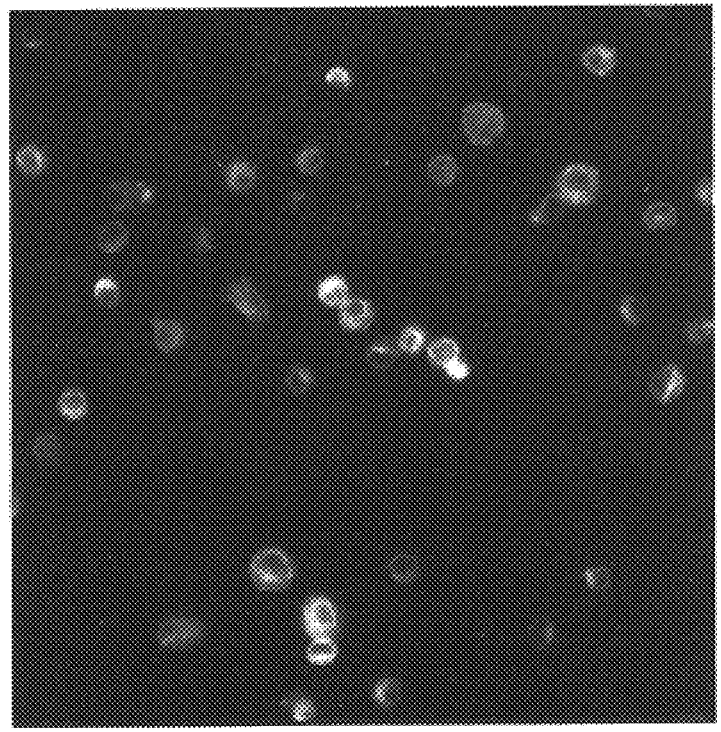
FIG. 8 is a digital image of adherent cells stained with tubulin indirect immunofluorescence stain on a biological sample preparation device, imaged with an Intelligent Imaging Innovations, Inc. digital confocal workstation equipped with a 40× Zeiss water immersion objective lens.

To visualize the results, the BSP device was placed in PBS and images were collected using an Intelligent Imaging Innovations, Inc. digital confocal workstation equipped with a 40× Zeiss water immersion objective lens. FIG. 8 shows that the BSP device of the present invention was successfully used in an immunofluorescent labeling protocol to stain CH12.LX cells for tubulin.

Example 7

The following Example demonstrates that two different staining chemistries (e.g., individual well sample preparation steps such as unique fluorescent marker treatments) can be performed simultaneously on a single device, a requirement for flexible high throughput.

This experiment was designed to confirm that samples attached to separate biological support members can be stained separately without reagent mixing. As described above, the two stains used in this experiment, FITC-WGA and Hoechst, show very different staining patterns and are optically separable with the correct filters. As in the previous examples, individually stained coverslips were used as a control for proper staining.

CHI2.LX cells were plated on poly-D-lysine coated BSP device cylinder ends and coverslips as described in Examples 2 and 4. The cells on the BSP device and coverslips were fixed as described previously in Example 4. After removing the fixative by aspiration, the BSP device and coverslips were extensively washed in phosphate buffered saline (PBS) as in Example 4. Also as described in Example 4, the BSP device and coverslips were treated with 0.2% Triton x100 in PBS for 5 minutes to permeabilize membranes. After further PBS washings as previously described, the BSP device and coverslips were incubated in DME tissue culture media+10% fetal calf serum for 20 minutes to reduce non-specific stain binding.

The individual cylinders of the BSP device were incubated in 20 µl of DME tissue culture media+10% fetal calf serum containing either 10 µg/ml Hoechst-33258 stain or 20 µg/ml FITC conjugated wheat germ agglutinin (Molecular Probes Inc., Eugene, Oreg.) for 1 hour. The incubation was performed in the individual wells of a 96 well plate and the wells alternated between WGA and Hoechst. Coverslips were incubated in 100 µl of either FITC-WGA or Hoechst solutions. As described in Example 4, the BSP device and coverslips were extensively washed and then soaked in PBS for 2 hours prior to observation.

The BSP device cylinder ends and coverslips were observed on an Intelligent Imaging Innovations, Inc. digital confocal workstation equipped with a 63× Zeiss water immersion lens, Nomarski optics, and appropriate Hoechst and FITC (ChromaTechnology Inc., Brattleboro, Vt.) filters as in Example 4. These filters are specifically designed to eliminate fluorescence bleedthrough of one probe into the other. Digital images from each condition were recorded for evaluation.

The cylinders of the BSP device were evaluated for Hoechst and WGA staining. To demonstrate that the BSP device performed correctly, each individual cylinder was selectively stained for either Hoechst or WGA only, but not both (data not shown).

The results showed that individual cylinder preparation steps are compatible with the BSP device, and further demonstrated that the BSP device is compatible with standard 96 well microtiter plates and reagent separation. Therefore, these experiments have shown that the BSP approach is useful in scenarios where the staining is different in separate samples.

Example 8

This Example demonstrates that the BSP device can be used to perform multiple labelings simultaneously and can be imaged at high resolution.

A variety of proteins have been shown to redistribute to the interface of a T cell/antigen presenting cell (APC) contact including: Talin (Kupfer et al., 1986), the microtubule organizing center (MTOC) (Kupfer and Dennert, 1984), Protein Kinase C Theta (Monks et al., 1997), the T cell receptor (TCR) (Kupfer and Singer, 1989), CD4 (Kupfer and Singer, 1989), and CD28 (Monks, 1995). The characterization of these redistributions required extremely high quality multi-labeling immunofluorescence and microscopic imaging.

In the present experiment, T cell/APC conjugates will be labeled for the above mentioned proteins using both a standard published method (i.e. with coverslips) and the BSP device and method. Given that the redistributions require very high quality, high magnification optics, this experiment will show that the BSP device and water immersion lens can be used for high resolution work.

Clonal D10.G41.1 (D10) (Kaye et al., 1983) T cells will be mixed with CH12.LX APCs that were pulsed overnight with conalbumin (the specific antigen for D10 cells) at a ratio of 1:1 and gently spun together to form conjugates. Conjugates will be incubated at 37° C. for 20 minutes and plated onto either two sets of poly-D-Lysine coated coverslips or a poly-D-lysine treated BSP device for 10 minutes at 37° C.

Coverslips and the BSP device will be fixed (3% paraformaldehyde, 3% sucrose, 1× PBS) for 10 minutes at room temperature as described in Example 4. Coverslips and the BSP device will be treated with 0.2% Triton x100 in PBS for 5 minutes to permeabilize membranes, also as described in Example 4. Coverslips and the BSP device will be incubated in DME tissue culture media+10% fetal calf serum for 20 minutes to reduce non-specific antibody binding. Individual coverslips will be incubated in one of a variety of primary antibodies: F500A2 hamster anti-TCR (Haskins et al., 1984), rabbit anti-PKC theta (Santa Cruz Biotechnology, Santa Cruz, Calif.), rabbit anti-talin (Kupfer et al., 1986), GK1.5 rat anti-CD4 (Dialynas et al., 1483), rabbit anti-tubulin (Kupfer et al., 1986), or 37.51 hamster anti-CD28 (Ledbetter and Herzenberg, 1979), for 1 hour at room temperature. The BSP device will be placed in a 96 well plate with each well containing one of the above mentioned antibodies.

Following the incubation, coverslips and the FPS device will be extensively washed in PBS as described in Example 4 above. Coverslips and BSP device cylinders that were incubated in either rat or hamster primary antibodies will be incubated in biotin conjugated donkey anti-rat or hamster (Jackson ImmunoResearch Laboratories, West Grove, Pa.) for 1 hour at room temperature. Coverslips and BSP device cylinders that were incubated in rabbit primary antibodies will be incubated in CY3 conjugated donkey anti-rabbit antibody (Jackson ImmunoResearch Laboratories, West Grove, Pa.) for 1 hour at room temperature. Following this incubation, coverslips and the BSP device will be washed extensively with PBS as described in Example 4.

Coverslips and BSP device cylinders that were incubated in a biotin conjugated secondary will be incubated in CY3 conjugated streptavidin (Jackson ImmunoResearch Laboratories, West Grove, Pa.) for 1 hour at room temperature. The remaining coverslips and cylinders will be incubated in blocking solution. The coverslips and BSP device will then be washed in PBS and soaked in PBS overnight to reduce background.

One set of coverslips will be mounted on slides and observed on an Intelligent Imaging Innovations, Inc. digital confocal workstation using a 40× Zeiss oil immersion objective. The other set of coverslips will be left in PBS and observed with a 40× Zeiss water immersion objective. The BSP device will be placed in PBS and each cylinder will be observed on the same workstation using a 40× Zeiss water immersion objective. Twenty fields from each staining condition will be imaged for stain evaluation.

Images from coverslips and from the BSP device will be scored for conjugate frequency (i.e. the number of conjugates vs. the number of single cells) and protein rearrangement within conjugates (i.e. MTOC rearrangement and clustering of PKC theta, TCR, LFA-1, CD4, and CD28). If the rearrangement frequencies of proteins within T cell/APC conjugates from the BSP device are similar (within a factor of two) to the frequencies scored from conjugates on coverslips, the experiment will be considered a success.

This experiment tests whether a single BSP device can be used to simultaneously prepare samples labeled for different molecules and image these molecules at state-of-the-art resolution. Successful completion of the experiment indicates that the BSP device is suitable for high resolution imaging applications at a high throughput.

The above experiments demonstrate that the BSP device and method is compatible with all aspects of fluorescent microscopy sample preparation including biology, wet chemistry, and observation optics. The evaluation criteria are straightforward and clear.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A method for preparing a biological sample for microscopy, comprising:
    (a) providing a biological sample preparation device comprising:
        (i) a substantially planar substrate having a top and a bottom surface; and,
        (ii) a plurality of biological support members projecting away from said top surface of said substrate and being arranged in an ordered array, each of said members having first and second ends, said first end having a surface effective for attachment of a biological sample thereto, and said second end connected to said top surface of said substrate at a predetermined angle;
    (b) attaching a biological sample to said first end of each of said members;
    (c) preparing said biological sample for microscopy by contacting said first ends with a series of reagents effective to visualize said biological sample by microscopy;
    (d) contacting said first ends that have said biological sample thereon with a medium; and,
    (e) visualizing said biological samples with a lens of a microscope.

2. The method of claim 1, wherein said first end is pretreated with a compound for enhancing attachment of said biological sample to said first end prior to said step (b) of attaching.

3. The method of claim 1, wherein said biological sample is a cell sample.

4. The method of claim 3, wherein said step of preparing includes the steps of fixing said cell sample, staining said cell sample, and washing said cell sample.

5. The method of claim 1, wherein said biological sample is selected from the group consisting of an intact cell, a cellular extract, a cellular membrane preparation, a tissue section and a nucleic acid molecule.

6. The method of claim 1, wherein step (b) of attaching comprises attaching a different biological sample to said first end of each of said members, and wherein step (c) of preparing comprises contacting each of said first ends with an identical series of reagents.

7. The method of claim 1, wherein step (b) of attaching comprises attaching the same biological sample to said first end of each of said members, and wherein step (c) of preparing comprises contacting each of said first ends with a different series of reagents.

8. The method of claim 1, wherein said microscopy is fluorescence microscopy.

9. The method of claim 1, wherein said lens of said microscope is a water immersion lens.

10. The method of claim 1, wherein said predetermined angle is about 90°.

11. The method of claim 1, wherein said first end is configured to interface with an objective lens of a microscope.

12. The method of claim 1, wherein said first end is substantially planar.

13. The method of claim 1, wherein said first end is configured to provide a surface area of at least about 1 mm$^2$ to which said biological sample can attach.

14. The method of claim 1, wherein said first end is configured to provide a surface area sufficient to attach at least about 100 cells thereto.

15. The method of claim 1, said members having dimensions such that said first ends can be contacted with a liquid medium in a manner such that said first ends are substantially equally exposed to said liquid medium.

16. The method of claim 1, wherein said second ends of said members are reversibly connected to said top surface of said substrate.

17. The method of claim 1, wherein said members are arranged on said substrate with respect to each other in a configuration which allows said first end of each of said members to be lowered into a separate well.

18. The method of claim 1, wherein said first and said second ends of said members are separated by a distance sufficient to allow said first end of each of said members to be contacted with liquid within a well without said second end being contacted by said liquid.

19. The method of claim 1, wherein said members are cylindrical.

20. The method of claim 19, wherein said first end is circular and wherein the diameter of said first end is at least about 0.3 mm.

21. The method of claim 1, wherein said members are frustoconical.

22. The method of claim 1, wherein said members are comprised of a material that is not fluorescent.

23. The method of claim 1, wherein said device comprises 96 biological support members, said array configured so that each of said members can be placed into a separate well of a 96-well microtiter plate.

24. The method of claim 1, wherein said device has from about 6 to about 12 biological support members, said array configured so that each of said members can be placed into a separate well of a row of a 96-well microtiter plate.

25. The method of claim 1, wherein said device is configured to be handled by a micromanipulator.

26. The method of claim 1, wherein said substrate has at least one containment means extending around a periphery of said substrate that is sufficient to contain a liquid on said top surface of said substrate.

27. The method of claim 1, wherein said substrate has at least one prop means sufficient to support said device when inverted onto a planar surface such that said biological support members do not contact said planar surface.

28. The method of claim 1, wherein said substrate has a handling means sufficient for handling said device without contacting said substrate or said biological support members.

29. The method of claim 1, wherein said device comprises a means for identifying a specific biological support member on said device.

30. The method of claim 29, wherein said means for identifying is selected from the group consisting of a bar code, a number, a letter, a color, and a symbol.

31. The method of claim 1, wherein said biological support member comprises a means for encoding a point of origin on said member for positioning on an X-Y stage of a microscope.

32. The method of claim 1, wherein said device is sterilizable.

33. The method of claim 1, wherein said device is disposable.

34. A method to clone and screen cells using a single device, comprising:
 (a) providing a biological sample preparation device comprising:
  (i) a substantially planar substrate having a top and a bottom surface; and,
  (ii) a plurality of biological support members projecting away from said top surface of said substrate and being arranged in an ordered array, each of said members having first and second ends, said first end having a surface effective for attachment of a biological sample thereto, and said second end connected to said top surface of said substrate at a predetermined angle;
 (b) attaching about one cell to be cloned to said first end of each of said members;
 (c) contacting said cell with a cell culture medium;
 (d) culturing said cell under conditions sufficient to allow growth and division of said cell into a clonal population of cells, such that said cell divides to produce at least about 100 cells;
 (e) preparing said cells for microscopy by contacting said cells with a series of reagents effective to visualize said cells by microscopy;
 (f) contacting said cells with a medium for microscopy; and,
 (g) visualizing said cells with the lens of a microscope to screen said cells for a selection characteristic.

* * * * *